US00PP31175P2

(12) United States Plant Patent
Cho

(10) Patent No.: US PP31,175 P2
(45) Date of Patent: Dec. 3, 2019

(54) ***COLOCASIA* PLANT NAMED 'MAUI SUNRISE'**

(50) Latin Name: *Colocasia esculenta*
Varietal Denomination: Maui Sunrise

(71) Applicant: John J. Cho, Kula, HI (US)

(72) Inventor: John J. Cho, Kula, HI (US)

( * ) Notice: Subject to any disclaimer, the term of this patent is extended or adjusted under 35 U.S.C. 154(b) by 0 days.

(21) Appl. No.: 16/350,580

(22) Filed: Dec. 3, 2018

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Barbara Campbell; James M. Weatherly; Cochran Freund & Young LLC

(57) ABSTRACT

A new cultivar of *Colocasia* plant named 'Maui Sunrise' that is characterized by prolific basal branching and leaves which are mid-green in color except for a prominent contrasting white to cream-yellow central streak.

2 Drawing Sheets

Genus and species: *Colocasia esculenta.*
Variety denomination: 'Maui Sunrise'.

BACKGROUND OF THE NEW PLANT

The present invention relates to a new and distinct variety of *Colocasia* commonly known as the taro plant or elephant ears. *Colocasia* is grown as a food crop and for use as an ornamental plant in containers or in the landscape. The new cultivar is known botanically as *Colocasia esculenta* and will be referred to hereinafter by the cultivar name 'Maui Sunrise'.

*Colocasia* is a tuberous rooted perennial which is native to tropical Asia and Polynesia. Native plants of *Colocasia* grow to 1.5 m to 2 m in height from starchy tubers. The leaves of *Colocasia* are heart-shaped and typically are very large in size.

The new *Colocasia* variety named 'Maui Sunrise' is the product of a formal breeding program carried out by the inventor in a cultivated area in Paia, Hi. The purpose of the breeding program is to develop new commercial varieties by combining attributes not found in currently commercially available varieties.

'Maui Sunrise' is a seedling selection from the controlled pollination of unreleased and unpatented varieties raised during the breeding program, namely breeding line '2007A-51' as the male parent, and breeding line '2007A-4' as the female parent. The inventor selected 'Maui Sunrise' in 2008.

'Maui Sunrise' exhibits a vigorous but compact plant habit with multiple basal branches giving rise to a high leaf count. The leaves of 'Maui Sunrise' are mid-green in color except for a prominent contrasting white to cream-yellow central streak.

The most commonly employed means of asexual propagation of the genus *Colocasia* is the excision and replanting of a shoot which consists of the apical 1 cm to 2 cm portion of the plant corm with the attached basal 15 cm to 20 cm portion of the petiole. In regions of the world where *Colocasia* is grown, this plant shoot is known as a "huli", and the means of propagation is known as "huli propagation", whereby the apical shoots are separated from the plant by cutting the shoot at the top of the corm immediately above the newest leaf scar and planted. The inventor first propagated 'Maui Sunrise' by the method of huli propagation in 2008 in Paia, Hi. Evaluation in field and pot studies have confirmed that the unique features of 'Maui Sunrise' are stable and uniform, and that 'Maui Sunrise' reproduces true to type in successive generations of asexual propagation by huli propagation and by tissue culture.

SUMMARY

The following traits have been repeatedly observed and represent the distinguishing characteristics of the new *Colocasia* cultivar 'Maui Sunrise'. These traits in combination set 'Maui Sunrise' apart from all other existing varieties of *Colocasia* known to the inventor. 'Maui Sunrise' has not been tested under all possible conditions and phenotypic differences may be observed with variations in environmental, climatic and cultural conditions, however, without any variance in genotype.

1. 'Maui Sunrise' grows vigorously while remaining compact with prolific basal branching and high leaf count.
2. The first three or four leaves of 'Maui Sunrise' are entirely mid-green in color except for slight white to cream-yellow coloration around the central vein or midrib. This coloration does not extend into the lamina of the first three or four leaves.
3. Subsequent leaves on a mature plant of 'Maui Sunrise' are mid-green in color, except for a prominent contrasting central streak which is white to cream-yellow in color and which extends along the lateral veins and into the adjacent leaf lamina.
4. Where present, the white to cream-yellow coloration along and around the veins is evident on both leaf surfaces.
5. The leaves of 'Maui Sunrise' are presented slightly folded along the midrib.

6. The petioles of the leaves of 'Maui Sunrise' emerge green in color and become grey-purple towards attachment to the leaf.
7. The upper surface of the leaves of 'Maui Sunrise' are glossy; the lower surface of the leaves are matte.

BRIEF DESCRIPTION OF THE PHOTOGRAPHS

The accompanying color photographs illustrate the overall appearance of 'Maui Sunrise' showing the colors as true as it is reasonably possible to obtain in colored reproductions of this type. Colors in the drawing may differ from the color values cited in the detailed botanical description, which accurately describe the actual colors of the new variety 'Maui Sunrise'.

Figure 1:
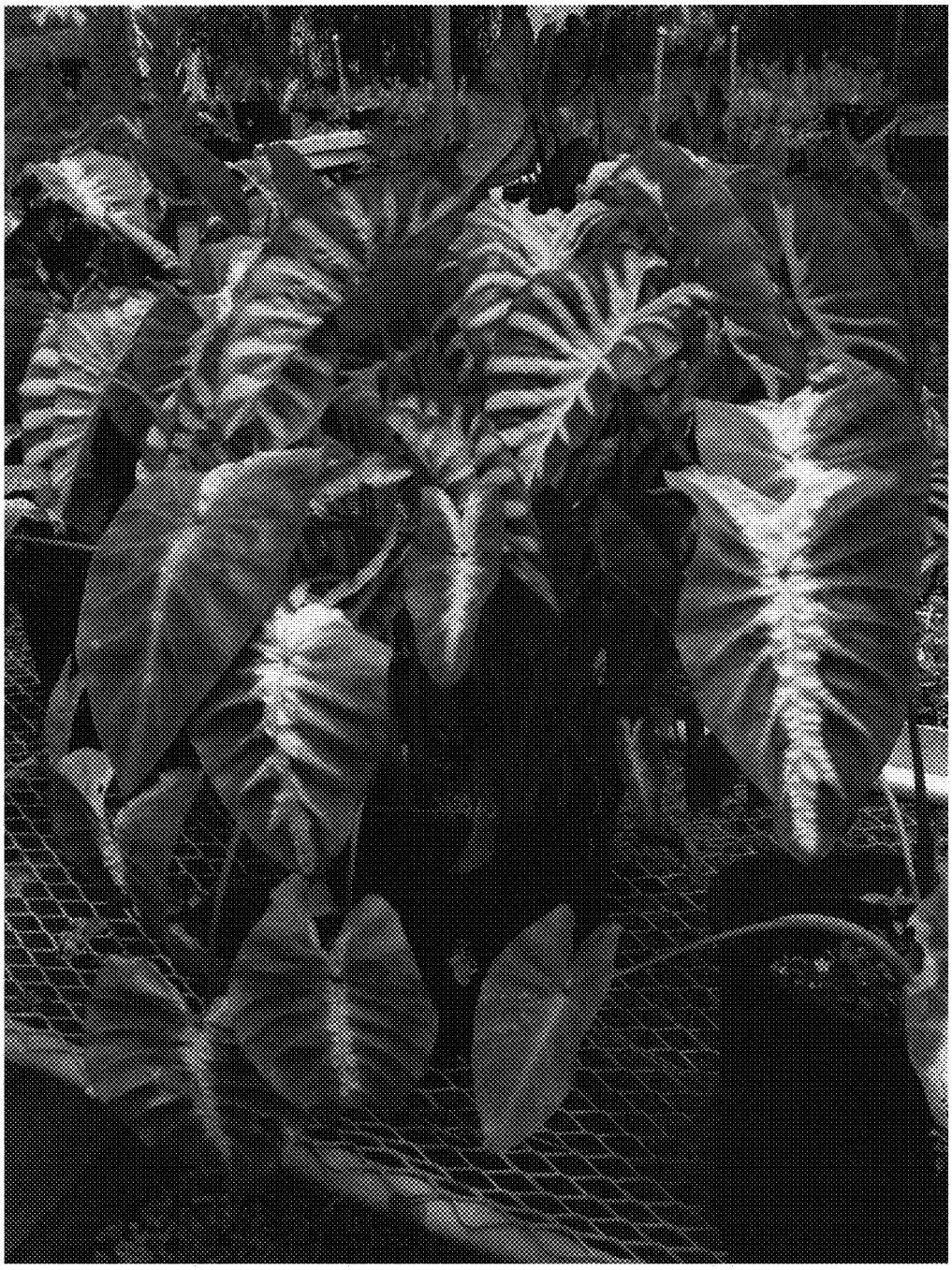
FIG. 1 shows a mature plant of 'Maui Sunrise'.
Figure 2:
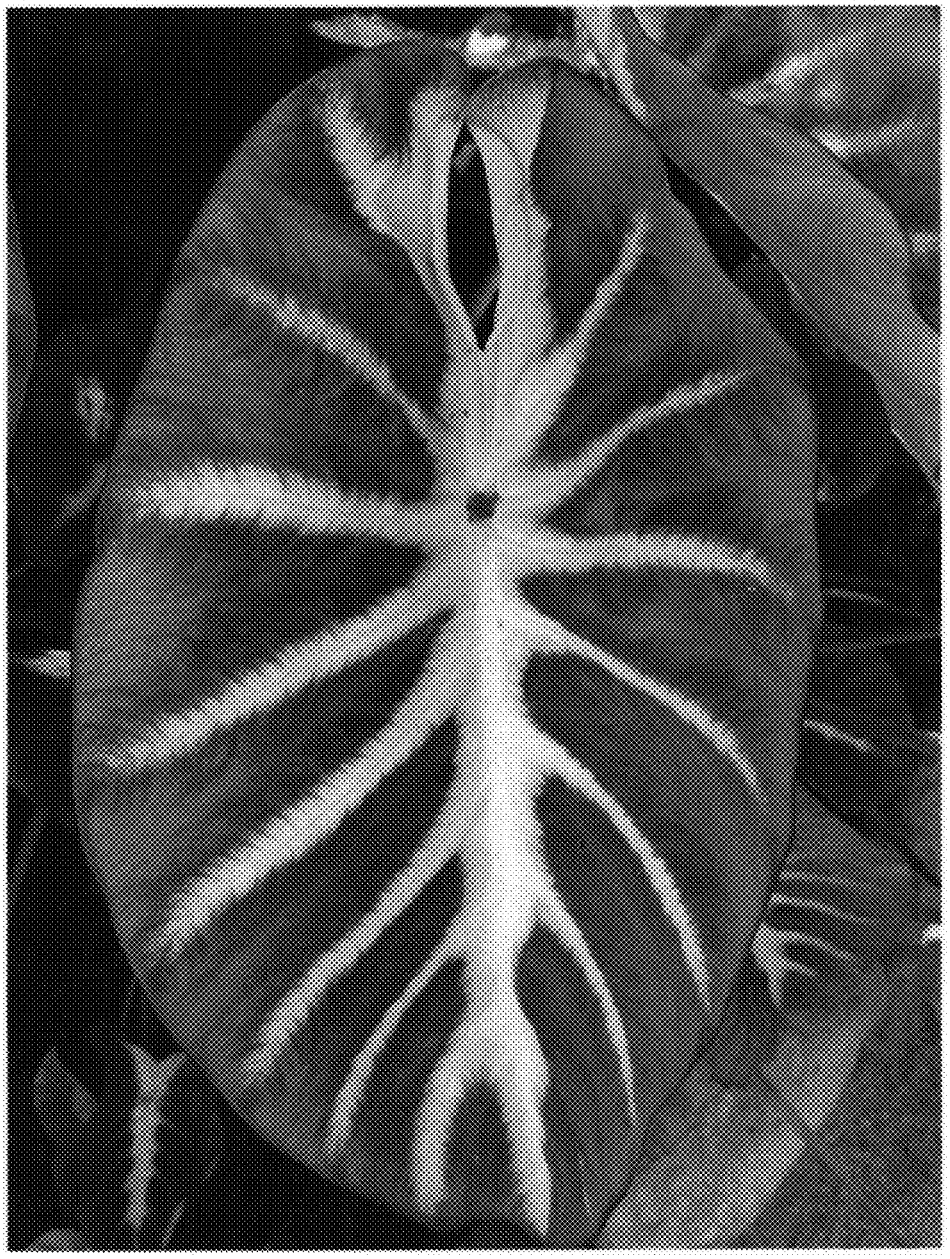
FIG. 2 shows a close-up of the leaf of 'Maui Sunrise'.

The photographs were made from a plant which is approximately 24 months old from a tissue culture division and which had been grown outdoors in Oxnard, Calif. No growth regulators had been applied.

BOTANICAL DESCRIPTION OF THE PLANT

The following is a detailed description of the new *Colocasia* plant named 'Maui Sunrise'. Data was collected from a mature plant which was 24 months old and grown outside in a 5-gallon container in Oxnard, Calif. The color determinations are in accordance with the 2007 edition of The Royal Horticultural Society Colour Chart, London, England, except where general color terms of ordinary dictionary significance are used. The growing requirements are similar to other *Colocasia*.

Botanical classification:

*Genus.*—*Colocasia.*

*Species.*—*esculenta.*

*Variety.*—'Maui Sunrise'.

*Common name.*—Taro or elephant ears.

Parentage:

*Male parent.*—Proprietary breeding line '2007A-51' (unreleased, unpatented).

*Female parent.*—Proprietary breeding line '2007A-4' (unreleased, unpatented).

Plant description:

*Use.*—Container or landscape plant.

*Cultural requirements.*—In common with all *Colocasia*, 'Maui Sunrise' thrives in high temperatures (above 70° F.), in full sun or partial shade, and is most vigorous when well-watered.

*Root system.*—Tuberous.

*Roots.*—Fleshy, up to 4 mm in diameter, with fibrous and fine lateral roots; color 155B.

*Root development.*—At soil temperatures 20° C. to 25° C., root initials are evident within 3 days. Roots will reach the edge of a 1 gallon container in 14 days.

*Plant vigor.*—Vigorous basal branching, forming dense canopy of leaves and stems.

*Plant growth habit.*—Upright, domed, non-spreading.

*Plant growth rate* (*crop time*).—A one gallon container plant may be produced in 12 to 16 weeks from a 4 cm cell transplant. A large specimen plant of 'Maui Sunrise' may be grown in a 5-gallon container in 24 months from a 4 cm cell transplant.

*Plant description.*—Once a huli or corm is introduced into the soil and the plant is established, additional corms or cormels are produced, attached to the original corm. These cormels give rise to new lateral shoots. A one year old plant of 'Maui Sunrise' produces 25 to 35 lateral shoots. Lateral shoots begin to appear above soil level about 6 to 8 weeks after planting of the initial plant.

*Corm* (*formed at base of each petiole or huli*).—Shape and dimensions: Short cylindrical, 2 cm to 3 cm in diameter, 1 cm in height. Surface texture: Rough with root initials (eyes). Color ranges between N186A and 202A.

*Cormels* (*arising from established corm, forming base of new lateral shoot*).—Shape and dimensions: Short cylindrical, 1.0 cm to 2.5 cm in diameter, 0.5 cm in height. Surface texture: Rough with root initials (eyes). Color ranges between N186A and 202A.

*Plant dimensions.*—75 cm to 90 cm in height and 60 cm to 75 cm in width.

*Plant hardiness.*—USDA Zone 7b.

*Propagation.*—Propagation is accomplished by huli propagation and by tissue culture.

*Time to develop daughter plants.*—Appear above soil around 2 to 3 months after planting.

*Crop time.*—1.5 to 2.5 months.

Foliage (lateral shoots):

*Petioles.*—Shape: Round section. Petiole tapers towards leaf attachment. Length: 30 cm to 45 cm. Diameter: 5 mm (just below attachment to lamina), 6 mm (at the upper sinus), 10 mm (at the middle of the sinus). Strength: Strong, arches under the weight of the leaf. Color: Emerges 146C becoming 181B approximately halfway towards leaf attachment. Surface texture: Glabrous, semi-glossy. Sap color: Colorless.

*Leaf.*—Number: Each lateral shoot bears 1 to 5 leaves at a time. Observed plant has 50 to 60 leaves of all ages. Dimensions at maturity: 40 cm in length and 25 cm in width. Average leaf sinus depth (mature leaf): 7 cm. Attitude: Oblique. Aspect: Erect with apex down. Leaf folded along vein midrib until flat when fully mature. Shape: Sagittate. Margins: Entire, slightly undulating. Margin color: 181B. Apex: Acute. Base: Peltate. Attachment: Petiolate with characteristic tissue formed at junction of leaf blade with the upper termination of the petiole. This area of the leaf tissue is also known as the "piko" and is evident by virtue of its upper surface color being similar to the color of the petiole. The principal veins radiate from the piko. Piko color: 185A. Leaf sheath: Open. Leaf surface: Adaxial surface: glossy; abaxial surface: Matte. Leaf color (both surfaces except central white to cream-yellow streak): Ranges between 139B and 136B. Leaf color (both surfaces, white to cream-yellow streak): Ranges between NN155D and 10C. Presence of white to cream-yellow streak: Not present on either surface of first 3 or 4 leaves of each lateral shoot. From third or fourth leaf, white to cream-yellow streak increasingly evident on both surfaces. Arrangement and dimensions of white to cream-yellow streak (mature leaf on mature plant): Adaxial surface: Dagger-shaped, extending from leaf base (pair) along central vein and partially along lateral (secondary) veins and extending into adjacent leaf lamina. Streak extends almost (within 1 cm) to leaf apex. Length: 40 cm. Width (leaf base): 7 cm to 9 cm. Abaxial surface:

Prominent, extends along abaxial midrib surface and along each abaxial lateral vein. Extends parallel to vein into leaf lamina, extending approximately 2 cm on either side of the lateral vein. Venation: Palmate. Veins: Three principal veins radiating from the piko, one midrib extending 30 cm from the piko to the tip of the lamina, and one pair of veins extending towards each of the basal lobe margins. Up to eight pairs of secondary veins radiating from the region of the piko and from the midrib. Vein color (adaxial surface): Ranges between 194B and 138B. Vein color (abaxial surface): Fine line 187A.

Inflorescence, flowers, reproductive organs and seed: The inflorescence arises from the leaf axils. The inflorescence is made up of a short peduncle, a spadix, and spathe. The spadix is botanically a spike, with a fleshy central axis to which the small sessile flowers are attached. The spadix is 9.5 cm to 10 cm long, with female flowers at the base, male flowers towards the tip, and sterile flowers in between, in the region compressed by the neck of the spathe. The extreme tip or appendage of the spadix has no flowers at all. The spathe is a large yellowish bract, 19.5 cm to 21.5 cm long, which sheathes the spadix. The lower part of the spathe is light-green (150B) in color and wraps tightly around the spadix and completely occludes the female flowers from view. The top portion of the spathe is yellow (13C) in color and is rolled inward at the apex, but is open on one side to reveal the male flowers on the spadix. The top and bottom portions of the spadix are separated by a narrow neck region, corresponding to the region of the sterile flowers on the spadix.

*Seed*.—Seed is not produced naturally since male and female flowers within each inflorescence do not mature at the same time.

Diseases and pests: In common with *Colocasias* in general, 'Maui Sunrise' is susceptible to attack by *Tetranychus urticae*, commonly known as red spider mite. Otherwise, the inventor has not observed that 'Maui Sunrise' is more or less susceptible to pests or diseases than other cultivars of the genus.

COMPARISON WITH PARENTAL LINES

The male parent, '2007A-51', exhibits chartreuse colored leaves with a glossy surface and white veins and leaf markings. The female parent, '2007A-4', exhibits green leaves with a glossy surface and white veins and leaf markings. Neither parent exhibits the white to cream-yellow streaking of the foliage of 'Maui Sunrise', nor the basal branching and highly clumping habit of 'Maui Sunrise'.

COMPARISON WITH KNOWN VARIETY

The closest comparison variety in commerce known to the inventor is *Colocasia* 'Nancy's Revenge' (unpatented) whose leaves are matte and bear a cream-yellow central streak which does not extend substantially along the veins and into the leaf lamina. In addition, the new shoots of 'Nancy's Revenge' arise from stolons which run from the mother plant, whereas the new shoots of 'Maui Sunrise' arise as basal shoots from the mother plant. In consequence, 'Maui Sunrise' grows with a dense clumping habit whereas the habit of 'Nancy's Revenge' is open and non-clumping. The mature height of 'Nancy's Revenge' is approximately 1.8 m., whereas the mature height of 'Maui Sunrise' is 90 cm.

I claim:

1. A new and distinct cultivar of *Colocasia* plant named 'Maui Sunrise' as described and illustrated herein.

* * * * *